US005891101A

United States Patent [19]
Wilcox et al.

[11] Patent Number: 5,891,101
[45] Date of Patent: Apr. 6, 1999

[54] SURGICAL SITE CHEMICAL DISPENSING SYSTEM

[75] Inventors: Todd Wilcox, Salt Lake City; E. Marlowe Goble; Alan Chervitz, both of Logan, all of Utah

[73] Assignee: MedicineLodge, Inc., Logan, Utah

[21] Appl. No.: 890,835

[22] Filed: Jul. 10, 1997

Related U.S. Application Data

[62] Division of Ser. No. 514,953, Aug. 14, 1995, Pat. No. 5,681,289.

[51] Int. Cl.$^6$ .................................................. A61M 5/152
[52] U.S. Cl. ............................................. 604/175; 604/93
[58] Field of Search ............................... 604/891.1, 175, 604/93, 258; 606/67; 623/22

[56] References Cited

U.S. PATENT DOCUMENTS

| | | | |
|---|---|---|---|
| 4,863,457 | 9/1989 | Lee | 604/891.1 |
| 5,059,175 | 10/1991 | Hanover et al. . | |
| 5,141,499 | 8/1992 | Zappacosta . | |
| 5,167,625 | 12/1992 | Jacobsen et al. . | |
| 5,169,389 | 12/1992 | Kriesel . | |
| 5,201,728 | 4/1993 | Giampapa | 604/891.1 |
| 5,372,583 | 12/1994 | Roberts et al. . | |
| 5,445,616 | 8/1995 | Kratoska et al. | 604/141 |

OTHER PUBLICATIONS

*The Journal of Arthroplasty*, vol. 6 No. 2 "Treatment of Acutely Infected Arthroplasty With Local Antibiotics" 2 Jun. 1991 Davenport, et al. pp. 179–183.
*Clinical Orthopaedics and Related Research*, No. 295, pp. 8–12 Oct., 1993 "Comparison of the Clinical Efficacy and Tolerance . . . " Blaha, et al.
*Clinical Orthopaedics and Related Research*, No. 295, pp. 37–42 Oct., 1993 "Gentamicin–Impregnated Polymethlmethacrylate Beads . . . " Evans, et al.
*Clinical Orthopaedics and Related Research*, No. 248, pp. 57–60, Nov. 1989 "The Results of Spacer Block Technique in Revision of . . . " Booth, Jr., et al.
*Clinical Orthopaedics and Related Research*, No. 295, pp. 3–7 Oct., 1993 "Penicillin as a Chemotherapeutic Agent" Chain, et al.
*Clinical Orthopaedics and Related Research*, No. 298, pp. 75–79 Jan., 1994 "Surgical Treatment of the Infected Hip Implant" Colyer, et al.
*Clinical Orthopaedics and Related Research*, No. 298, pp. 97–105 Jan., 1994 "Palacos Gentamicin for the Treatment of Deep . . . " Garvin, et al.
*Clinical Orthopaedics and Related Research*, No. 295, pp. 43–46 Oct., 1993 "Audiometric Thresholds in Osteomyelitis Patients . . . " Haydon, et al.

(List continued on next page.)

*Primary Examiner*—Robert A. Clarke
*Assistant Examiner*—Catherine Cogut
*Attorney, Agent, or Firm*—M. Reid Russell

[57] ABSTRACT

A surgical site chemical dispensing system for dispensing a liquid chemical agent, such as an antibiotic, anesthetic, growth factor, hormone, anti-neoplastic agent, or the like, directly onto a site of a surgical procedure. The system includes at least one bladder formed from a pair of thin sections of a flexible material to have an internal cavity that connects to an open tube wherethrough the liquid chemical agent is passed, under pressure, into the bladder. The liquid chemical agent passes, as a low volume flow, through at least one hole formed through a bladder section of material and onto the surgical procedure site. The invention includes a single or a pair of individual bladders that is or are each formed from a thin flexible biocompatible material, with each bladder for positioning in close proximity to a prepared bone surface with at least one and preferably a plurality of holes formed through a bladder section of material surface that is in engagement with the prepared bone surface to bleed a low volume flow of a chemical agent onto the bone surface.

5 Claims, 12 Drawing Sheets

OTHER PUBLICATIONS

*Clinical Orthopaedics and Related Research*, No. 295, pp. 47–53 Oct., 1993 "Long–Term Implantation of Gentamicin–Polymethylmethacrylate . . . " Henry, et al.

*Clinical Orthopaedics and Related Research*, No. 295, pp. 54–62 Oct., 1993 "The Antibiotic Bead Pouch Technique" Henry, et al.

*Clinical Orthopaedics and Related Research*, No. 295, pp. 63–76 Oct., 1993 "Antibiotic Bead Chaine" Klemm.

*Clinical Orthopaedics and Related Research*, No. 278 pp. 260–263 May, 1992 "Bacterical Adherence to Plain and Tobramycin–Laden . . . " Lyons, et al.

*Clinical Orthopaedics and Related Research*, No. 248 pp. 120–127 Nov., 1989 "Long–Term Results of Various Treatment Options . . . " Morrey, et al.

*Clinical Orthopaedics and Related Research*, No. 295, pp. 96–101 Oct., 1993 "A Comparison of Gentamicin–Impregnated Polymethylmethacrylate . . . " Nelson, et al.

*Total Joint Arthroplasty*, pp. 349–351 "The Economic Impact of Infected Total Joint Arthroplasty" Chapter 33 Sculco.

*Clinical Orthopaedics and Related Research*, No. 295, pp. 23–27 Oct., 1993 "The Treatment of Infected Nonunions With . . . " Calhoun, et al.

*The Journal of Bone and Joint Surgery, Incorporated*, vol. 75–A, May 1993 pp. 714–719 "Antibiotic–Leaching from Polmethylmethacrylate Beads"Seligson, et al.

*Clinical Orthopaedics and Related Research*, No. 299, pp. 169–172 Feb. 1994 "Treatment of Infected Total Knee Arthroplasty" Whiteside.

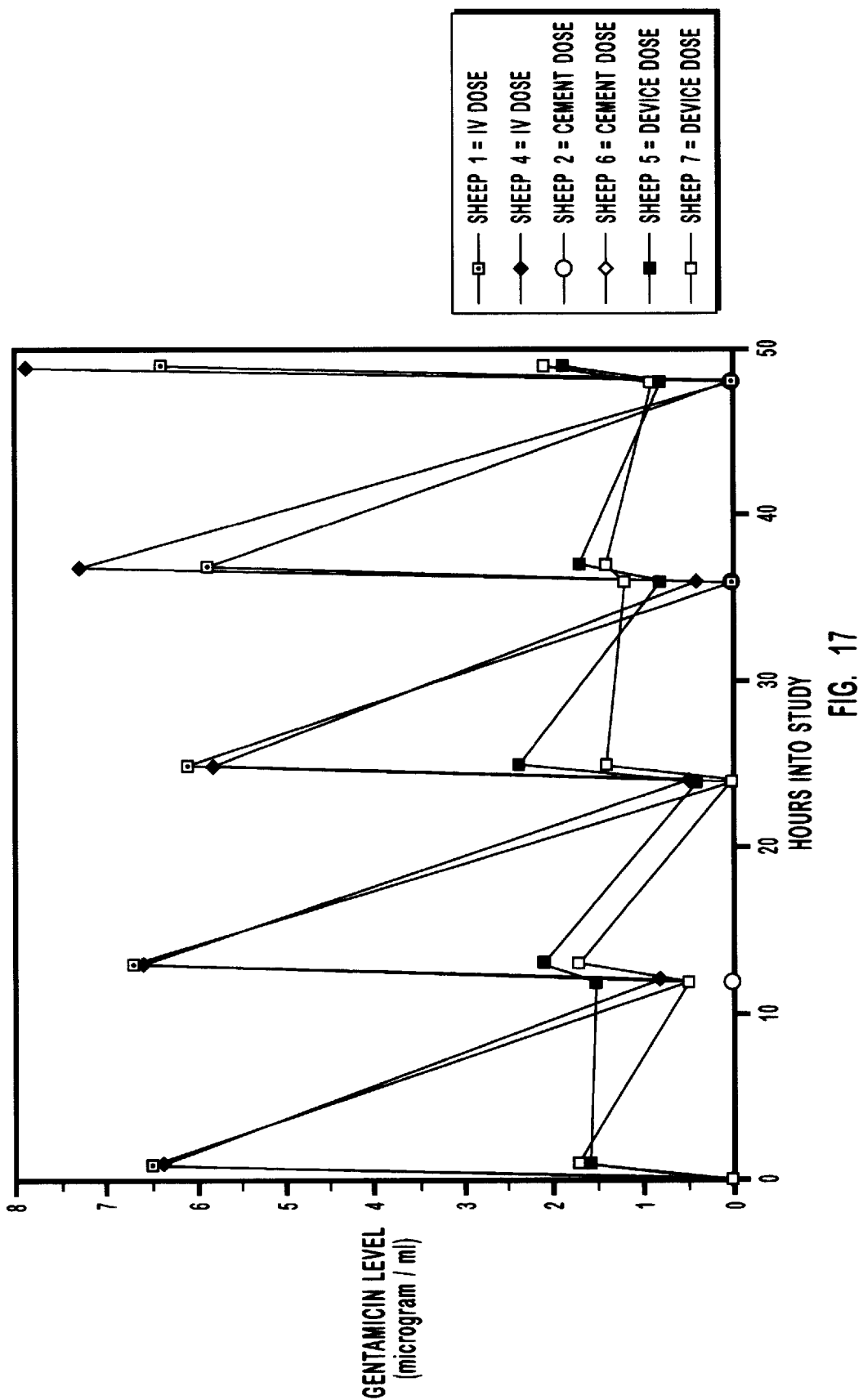

SURGICAL SITE CHEMICAL DISPENSING SYSTEM

This application is a division of appliaction Ser. No. 08/514,953, filed on Aug. 14, 1995 now U.S. Pat. No. 5,681,289.

BACKGROUND OF THE INVENTION

1. Field of the Invention

This invention relates to surgical devices and procedures for their use for implanting the surgical device in a patient during a surgical procedure to dispense a chemical to a site of that procedure for a period of time thereafter.

2. Prior Art

In a surgical procedure where a part of a human body is opened and a procedure performed thereon, it is common to apply an antibiotic, chemical deadening agent, growth stimulator, chemotherapeutic agent, radioactive isotope, or the like, onto the site of that procedure prior to closing to provide for infection control, pain control, and for other chemically-mediated biological response. In an orthopedic surgical procedure it is often necessary to open the skin to a bone surface or cortex to perform a procedure, such as one involving a joint replacement, fracture reduction, or the like, which bone site or location is particularly prone to infection after closure. Where such infection is present, often large to even massive doses of antibiotics are required to be taken, orally or by injection, to overcome such infection. Such doses themselves often create undesirable side effects.

The present invention, by providing for dispensing an appropriate chemical agent or agents to an actual site of such treatment, limits the amount of such chemicals as needed to overcome the infection or provide treatment, thereby minimizing the likelihood of unwanted side effects. In addition to passing an antibiotic, or like chemical, onto a surgical site, for infection control, or other treatment, the devices and procedures of the invention can also be used for dispensing a local anesthetic agent, or the like, to that site, to minimize a patient's discomfort during healing. Additionally, the invention can also be used to deliver local growth factors to the site to encourage healing, or chemotherapeutic agents to destroy unwanted cells, such as cancer cells.

Certainly, applications of chemical agent onto a site of a surgical procedure prior to closing are not new. Also, arrangements for providing a medication conduit to a potential injection site have been in use. For example, an article presented in "The Journal of Arthroplasty", titled, Treatment of Acutely Infected Arthroplasty With Local Antibiotics, Vol. 6, No. 2, dated June 1991, pages 179–183, sets out an implantable reservoir with a feed conduit into a surgical site is shown as having been used on a number of patients. Further, such an implantable reservoir and feed conduit connecting into the vena cava has been used as a substitute for a peripheral venous catheter to provide long term infusion support is currently in use and is known as a porta-cath or central line. Such other devices and arrangements, however, unlike the present invention, have not involved a range of implantable devices to be positioned directly on or closely adjacent to a site of infection, injury, or tumor, to pass a chemical agent therefrom. With the devices or the invention and methods for their use chemical agents can be delivered through a connecting line from a reservoir maintained at or just below the patient's skin surface. Further, such implants, as those of the invention can be made to be biodegradable to be absorbed by the body after removal of the transmission line.

SUMMARY OF THE INVENTION

It is a principal object of the present invention in a chemical dispensing system to provide a sump or bladder that is linked by a tube or other conduit to a reservoir to be implanted at or closely proximate to a site of a surgical procedure for dispensing a chemical agent through the sump or bladder to that site.

Another object of the present invention is to provide a sump or bladder of a chemical dispensing system that is shaped appropriately to be implanted between a bone surface and a prosthesis fitted thereto, or immediately adjacent to a broken bone or injured tissue area, to dispense a chemical agent thereto that is passed from a reservoir.

Another object of the present invention is to provide a sump or bladder or sumps or bladders of the chemical dispensing system for installation between a prepared bone end and a prosthesis, such as a knee or hip prosthesis component, to dispense a chemical agent directly onto the bone surface that has been passed from a reservoir through a connecting tube.

Another object of the present invention is to provide sump or bladder having the shape of a prosthetic implant, such as a stem, acetabular component, distal femoral knee component, or tibial tray that itself is formed to contain and dispense a chemical agent therefrom after such agent has been passed from a reservoir through a connecting tube.

Another object of the present invention is to provide a sump or bladder of a chemical dispensing system that is similarly shaped to a polyethylene insert as is used in a total joint surgical procedures and is formed to contain and dispense a chemical agent therefrom that has been passed from a reservoir through a connecting tube into a joint.

Another object of the present invention is to provide a sump or bladder that is arranged for fitting into to travel within and along a longitudinal passage an intramedullary rod or nail that is for insertion into a patient's intramedullary canal to a location that is opposite to a bone fracture whereat, by operation of a subcutaneous pump, a chemical agent is passed into the area of the bone break.

Still another object of the present invention is to provide a chemical agent dispensing pump and sleeve arrangement as part of an external fixation device for use for pinning to sections of a bone adjacent to a bone fracture and for maintaining the mechanical stability of that fracture and to pass a chemical agent into the bone during healing.

Still another object of the present invention is to provide a sump or bladder as a part of an implant device, such as a penile implant to be a part thereof and is connected through a tube to a reservoir and pump for passing a chemical agent to that implant to ward off infection during the healing process or to treat an infection that has developed.

Still another object of the present invention is to provide a sump or bladder or sumps and bladders with connecting tube or tubes, reservoir and pump whereby chemical agents can be delivered to a site to either encourage cell growth or to destroy undesirable cells, such as tumor cells.

Still another object of the present invention is to provide a number of combinations of sump or bladder or sumps or bladders, with a connecting tube or tubes, reservoir and pump as a chemical dispensing system where all or some of the implanted components can be formed of a biodegradable material to remain in and be absorbed by the body after healing.

Still another object of the present invention is to provide a chemical dispensing system that is conveniently installed in a patient along with a prosthesis or appliance to provide a controlled flow of a chemical agent, such as an antibiotic that may be a powerful antibiotic, such as gentamicin that, when administered conventionally such as by IV dosing, may cause an adverse reaction to a patient's kidneys or ears at high dosages, where, by delivery directly to the site of the surgical procedure an infection can be effectively treated without threat to the health of the patient's organs, or the like.

Principal features of the invention include a sump or bladder having one or more drip holes formed therein. The sump or bladder is cut or shaped, in several embodiments, to fit between a prepared bone end or section and a prosthesis fitted thereon. The sump or bladder is connected by a tube to a reservoir and pump arrangement. The reservoir and pump may be an implantable needle injection port, an exterior pump, or the like. For the needle injection port, a surgeon fits a hypodermic needle through the patient's skin into the implanted port and reservoir and, by operating the hypodermic plunger, forces a chemical agent through the tube and out of the sump or bladder hole or holes. Such chemical agent can be an antibiotic, a local anesthetic type chemical, degradative enzyme, growth stimulator, chemotherapeutic agent, radio active isotope, or the like, within the scope of this disclosure.

Alternative, the sump or bladder can be for fitting in an intramedullary rod or nail that includes a longitudinal cavity or slot, such that an opening or openings in the sump or bladder will align with the opening in the rod. The sump or bladder is designed for travel along the nail to be opposite to a bone fracture for the purpose of delivering a chemical agent from the sump or bladder through the longitudinal cavity or slot to the surrounding bone. To provide chemicals for this delivery the sump or bladder is connected through a tube to a reservoir and pump arrangement.

Further to the invention, a sump or bladder includes a hole or spaced holes therein formed to have a diameter to accommodate a chemical agent drip therethrough, which sump or bladder is shaped for inclusion with an implant device, such as a penile implant. Such bladder also connects through a tube to a reservoir and pump arrangement, that may be a hypodermic needle receiving port and reservoir for implanting in a patent, or the like, to pass a chemical agent, such as an antibiotic, topical anesthetic, other chemical agents, or the like, into the sump or bladder to be dispersed into the tissue at the implant site.

The bladder of the chemical dispensing system of the invention can be arranged to be removable after use, or all or parts thereof may be formed of a biodegradable material to stay in the patient after healing and be absorbed by the body. In such biodegradable sump or bladder, the tube is preferably connected to be pulled therefrom along with the reservoir and removed, leaving the biodegradable sump or bladder in place.

THE DRAWINGS

These and other objects and features of the invention in a chemical dispensing system will become more apparent from the following description taken in conjunction with the accompanying drawings that are presently regarded as presenting the best modes for carrying out the invention:

Figure 1:
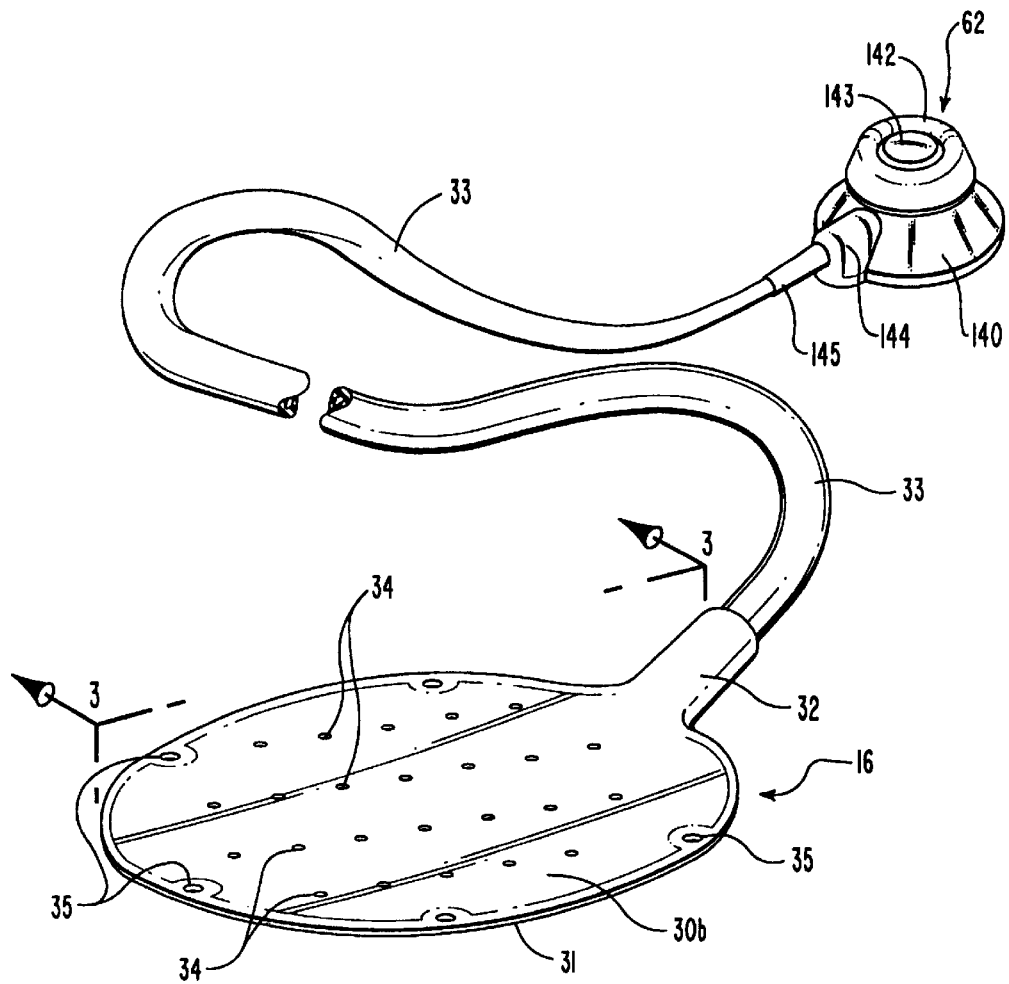
FIG. 1 is bottom plan perspective view of a tibial sump or bladder component and connected tube of a chemical dispensing system of the invention that is for fitting between a prepared proximal tibia surface and a tibial component of a knee prosthesis.
Figure 2:
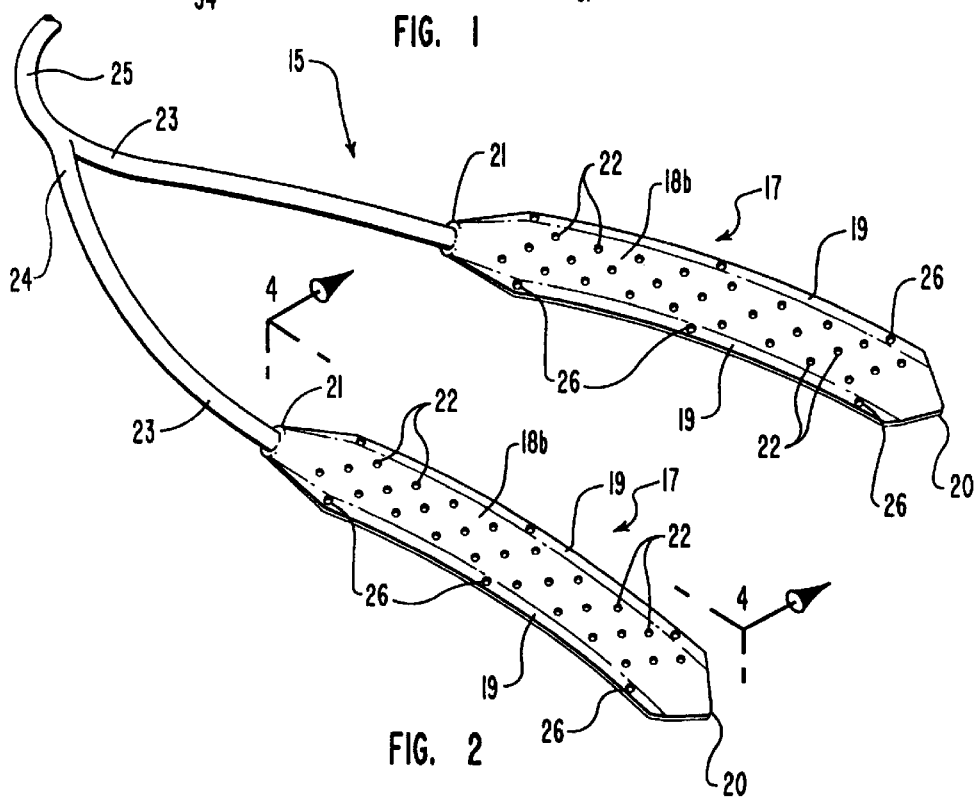
FIG. 2 is a bottom plan perspective view of a pair of femoral sump or bladder components and connected tubes of a chemical dispensing system of FIG. 1 that are for fitting between prepared distal femur surfaces and sections of a femoral component of a knee prosthesis.
Figure 5:
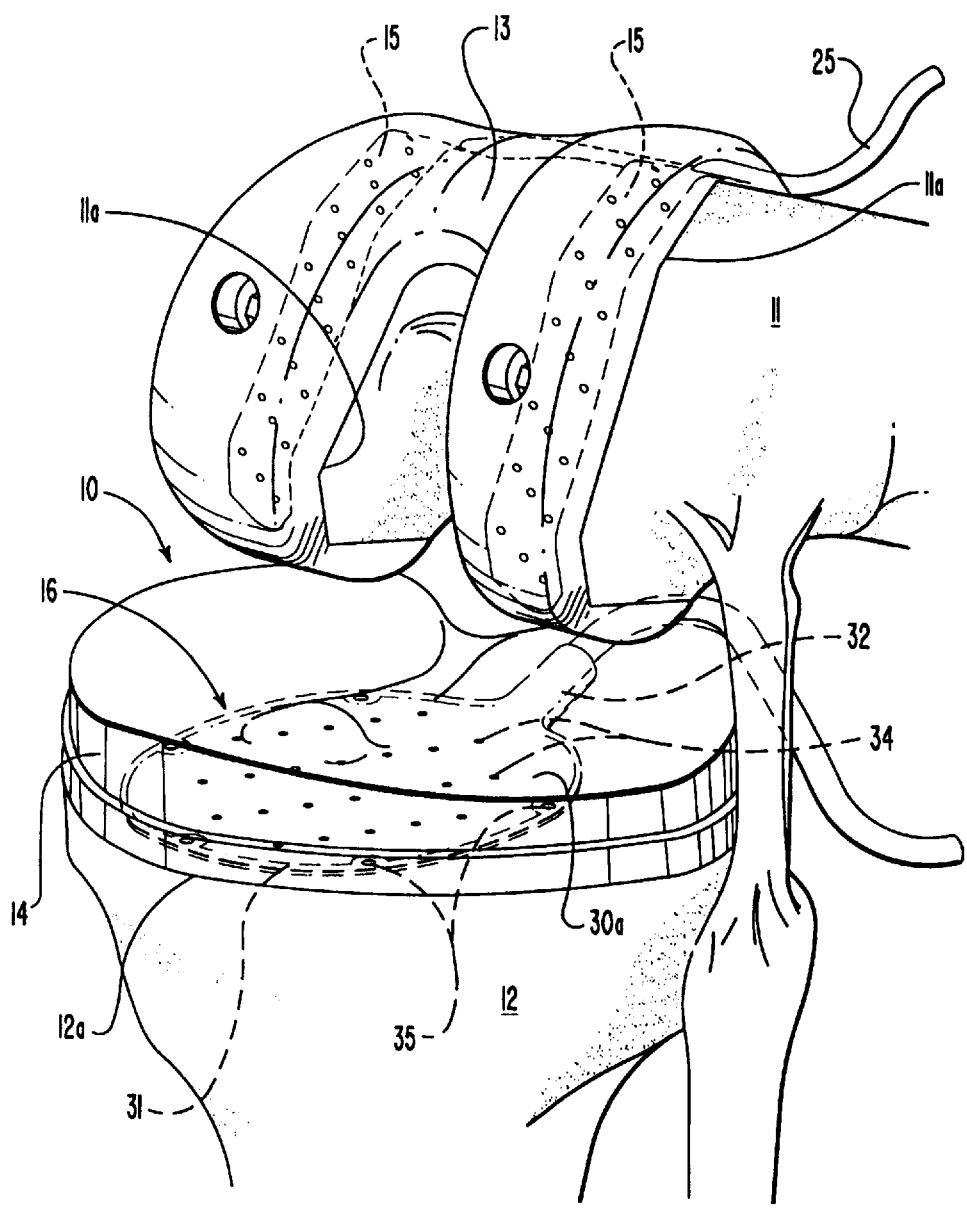
Figure 6:
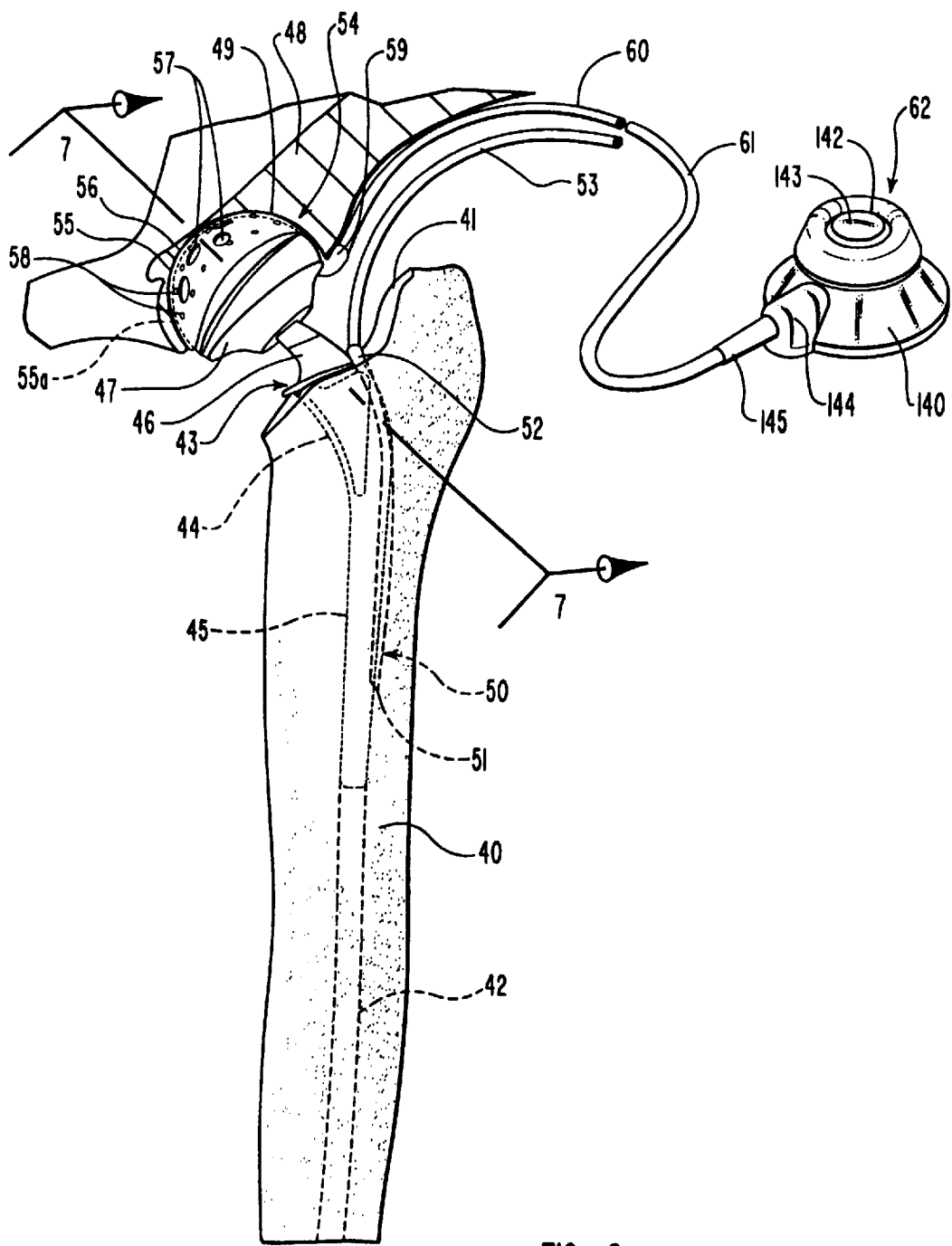
Figure 7:
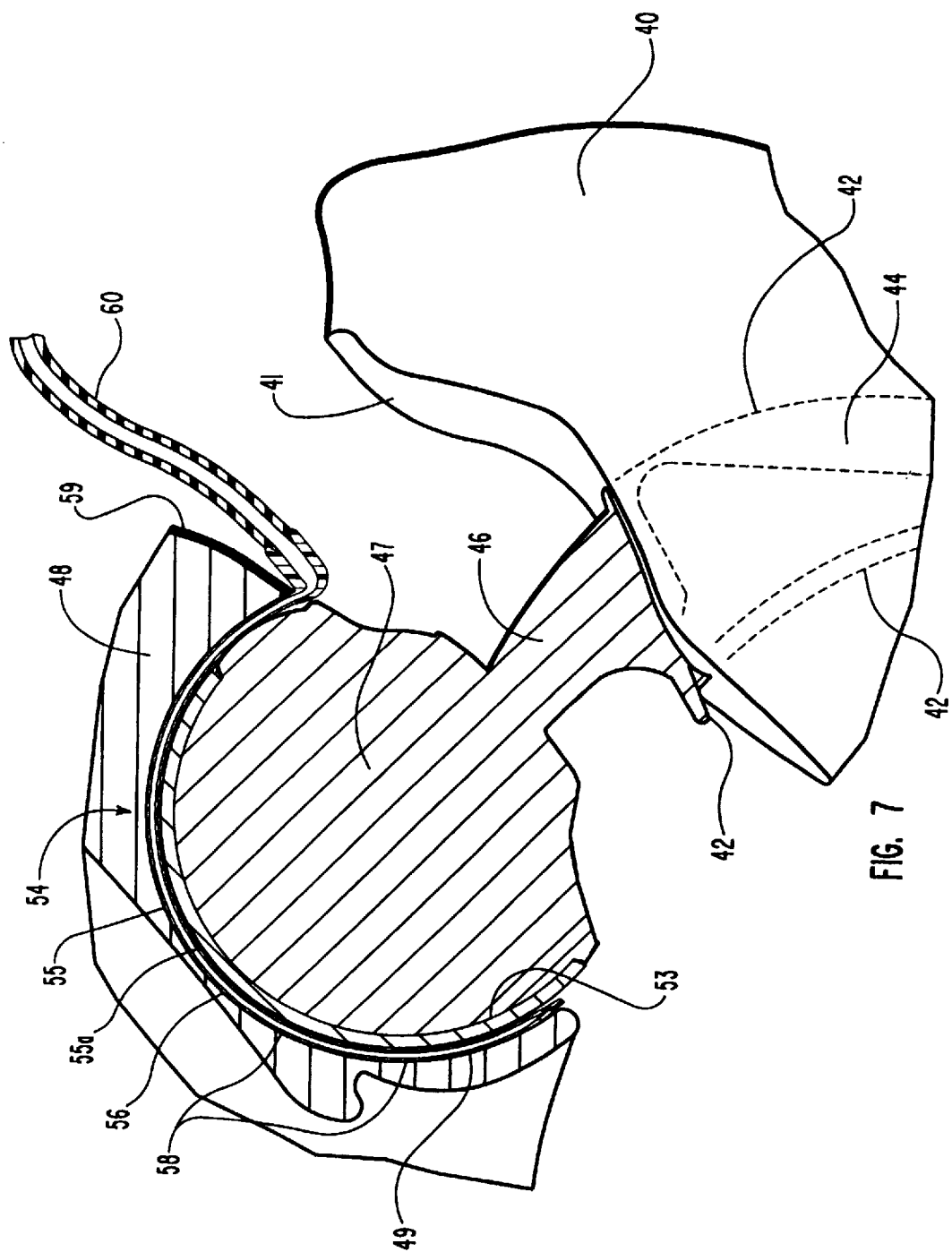
Figure 8:
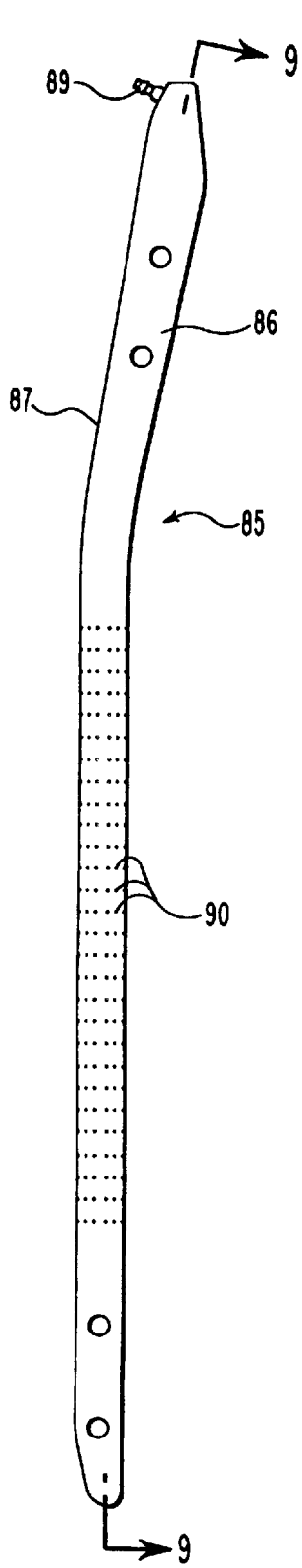
Figure 9:
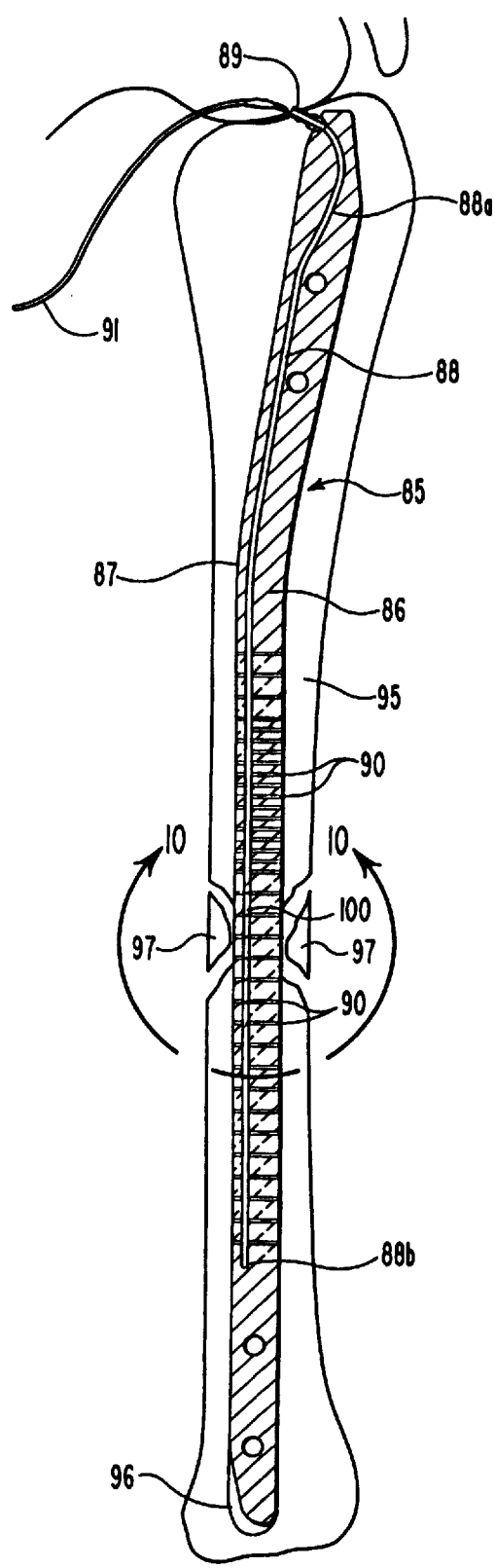
Figure 10:
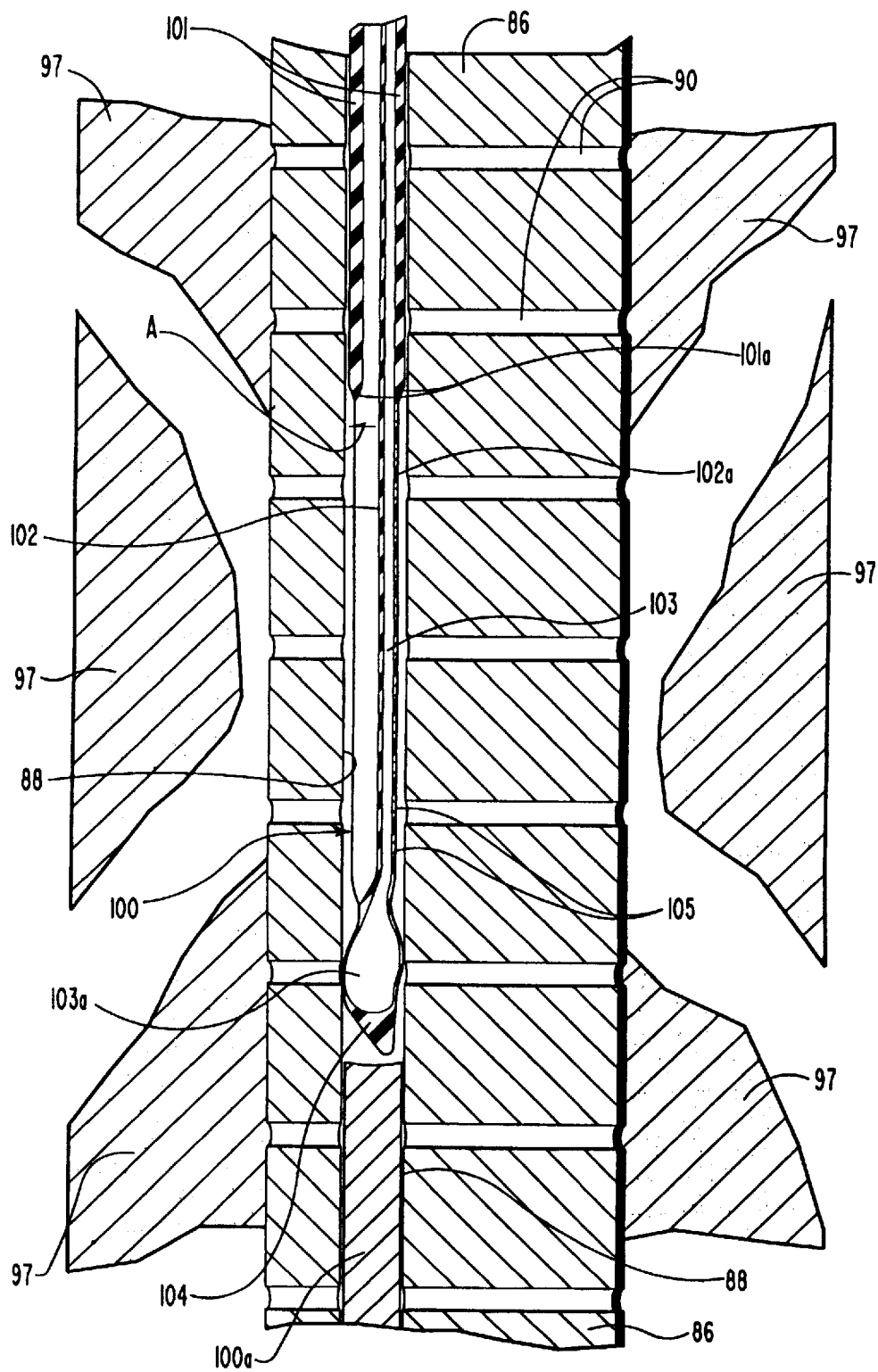
Figures 11, 12, 13:
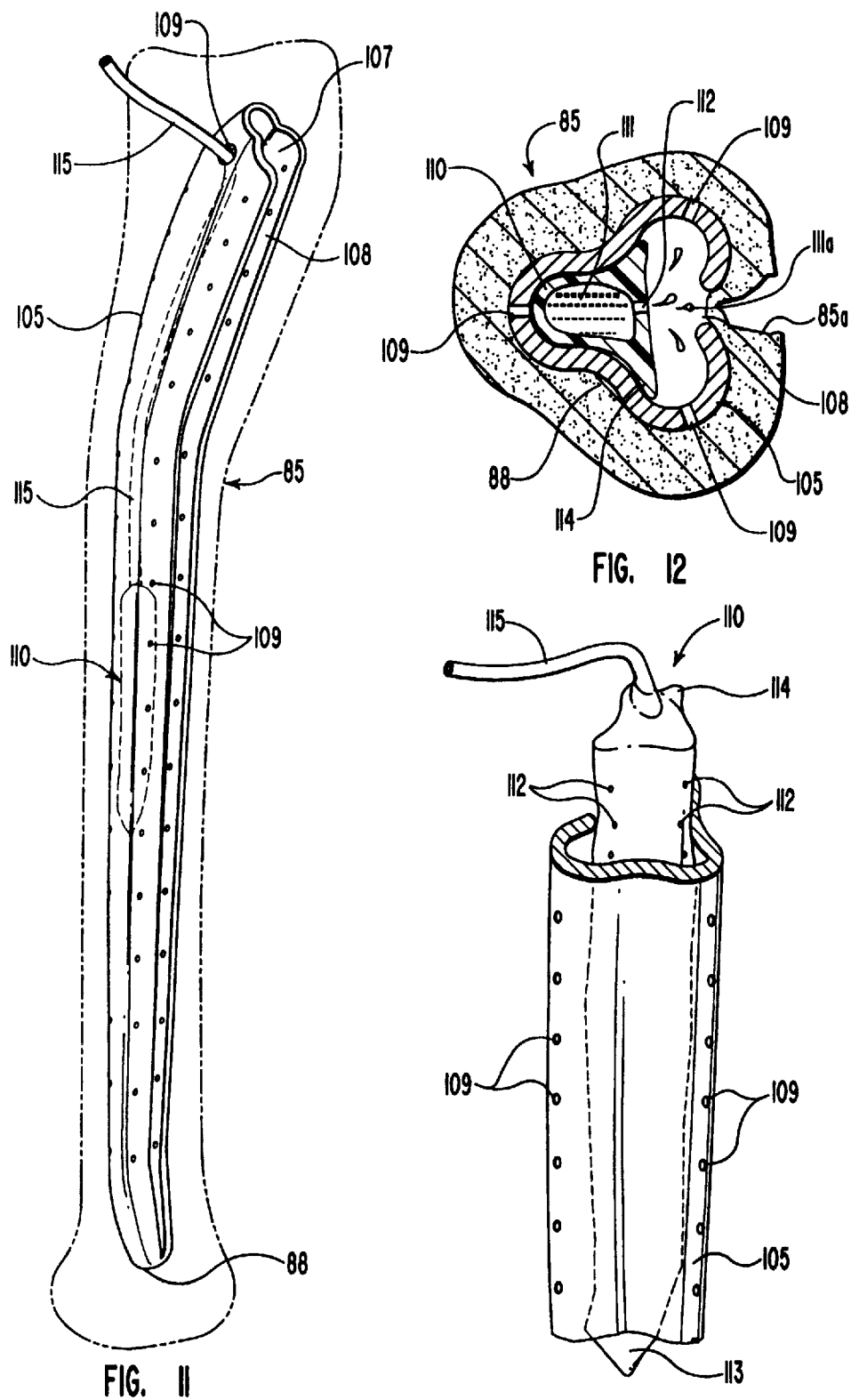
Figure 14:
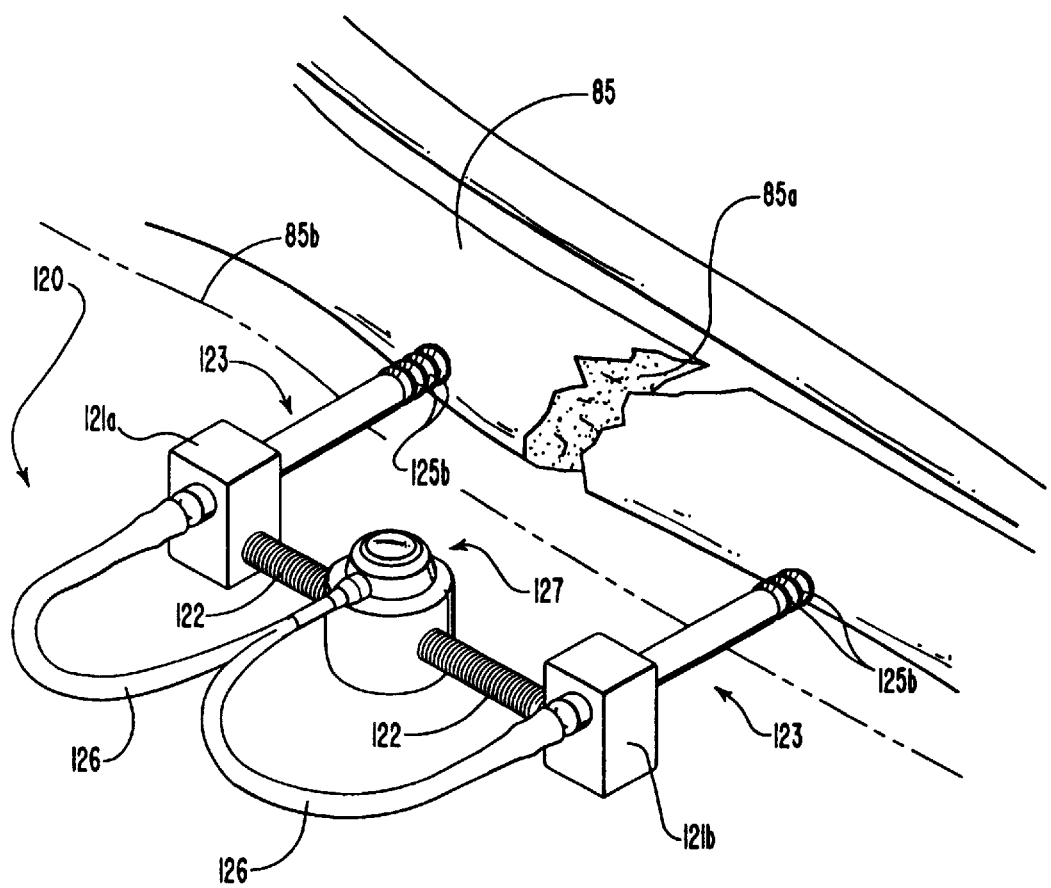
Figure 14A:
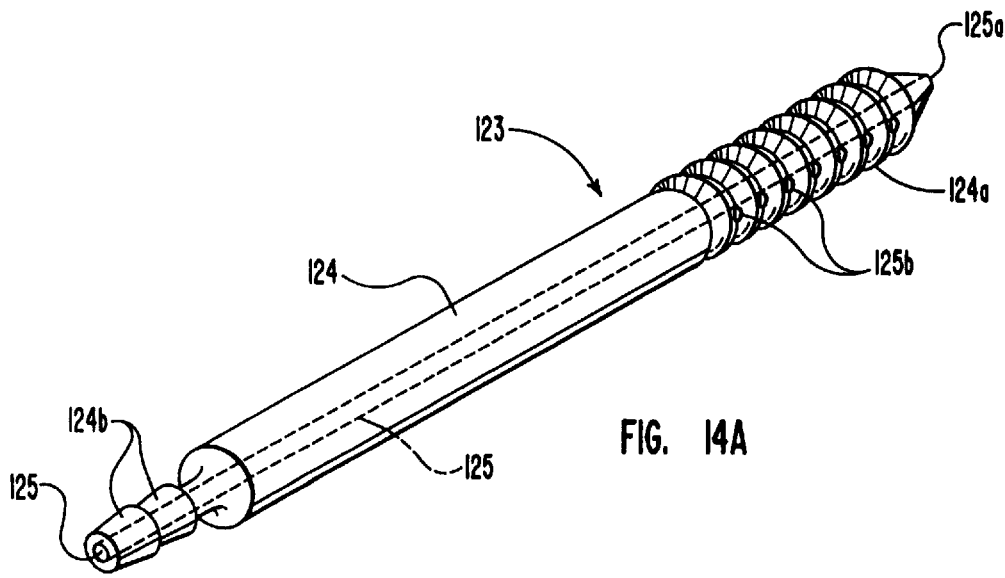
Figure 15:
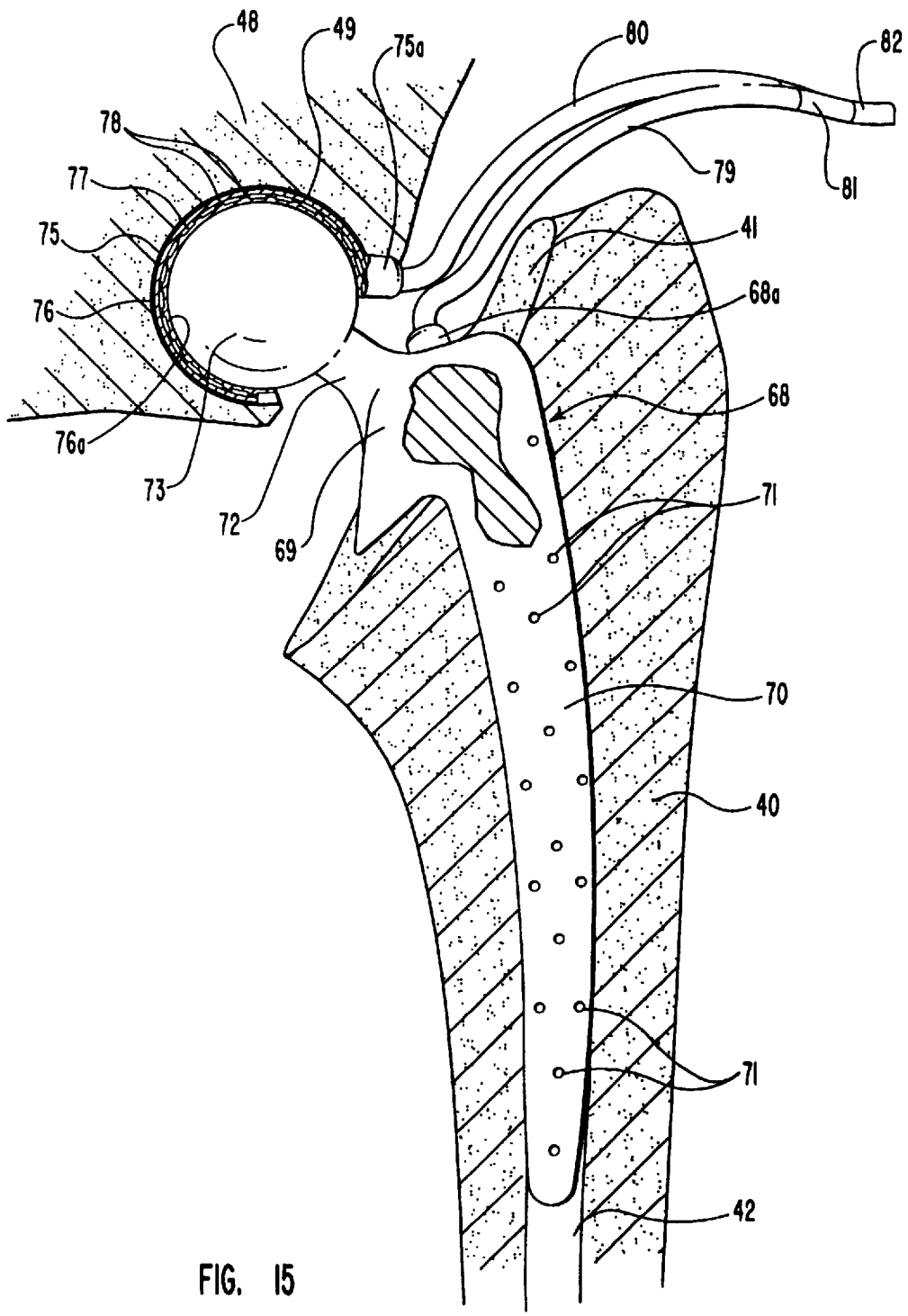
Figure 16:
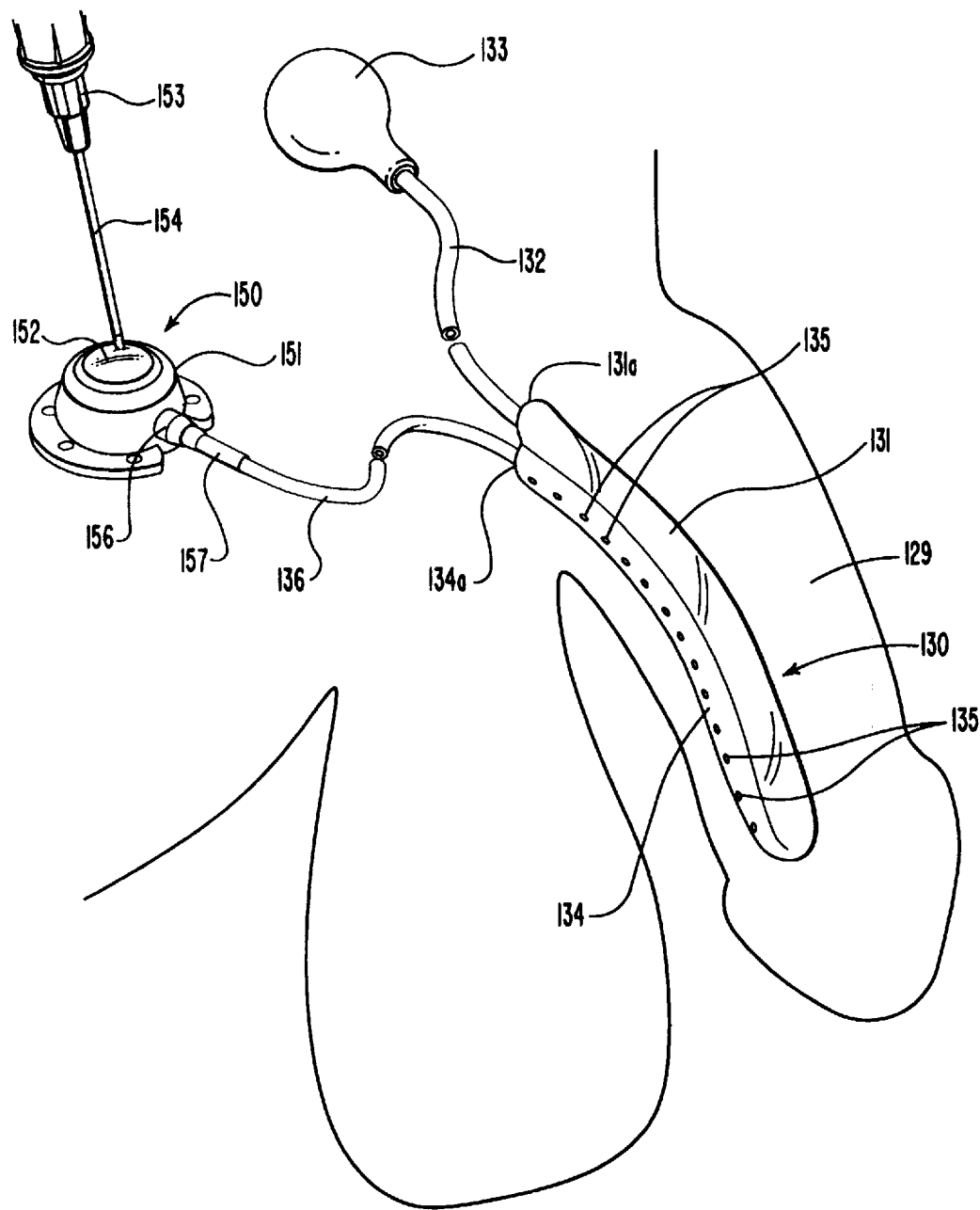

FIG. 5 is a side elevation perspective view of a patients knee whereto a knee prosthesis has been fitted after the distal femur and proximal tibia have been shaped appropriately and showing the tibial sump or bladder component of FIG. 1 in broken lines positioned between the proximal tibia prepared end and tibia component of the prosthesis, and showing the pair of femoral sumps or bladders of FIG. 2 in broken lines fitted between the prepared distal femur end and the femoral component of the prosthesis;

FIG. 6 is a side elevation view of a patient's hip and femur proximal end that has been cut and shaped to receive a stem portion of a hip prosthesis, and showing a broken away portion of the hip as a seat for a ball end of the prosthesis, and showing a cup shaped sump or bladder having holes formed therein that is arranged between the seat and hip bone with a tubular sump or bladder shown fitted alongside the prosthesis stem and against the bone surface in the femoral medullary channel and showing tubes connecting to which sumps or bladders and to a reservoir and pump arrangement;

FIG. 7 is an enlarged sectional view taken along the line 7—7 of FIG. 6;

FIG. 8 is a side elevation view of a shaft that is bent from the vertical at a top section and includes a fitting in its top end that connects, to pass fluid, into a shaft longitudinal passage that intersects with a number of spaced transverse passages;

FIG. 9 shows the shaft of FIG. 8 fitted into the tibia medullary channel and extending across a broken section thereof and showing a tube connected to the top fitting;

FIG. 10 is an enlarged sectional view taken within the line 10—10 of FIG. 9;

FIG. 11 is a side elevation view of an embodiment an intramedullary nail that is open longitudinally and includes a longitudinal slot therein, and showing a cylindrical sump or bladder with a plurality of holes formed therein that connect on a upper end to a tube that is fitted through a hole formed through the nail wall;

FIG. 12 is a cross sectional view taken along the line 12—12 of FIG. 11;

FIG. 13 is an enlarged side elevation perspective view of a section of the intramedullary nail of FIG. 11 showing the sump or bladder fitted therein and showing a number of spaced vertical holes formed through the nail lobes;

FIG. 14 is a profile perspective view of a patient's lower leg showing their tibia as broken with posts of a fracture fixation device shown fitted through their skin and turned into the tibia, above and below the break, which posts are shown to have holes formed therein proximate to their ends with tubes fitted onto which posts that connect through lines to an external reservoir and pump;

FIG. 14A shows an enlarged view of a tube with threaded end of the fracture fixation device of FIG. 14 removed therefrom;

FIG. 15 is a side elevation view of a section of a patient's proximal femur whose end has been removed for receiving a temporary hip prosthesis and showing a stem thereof that has had a section removed to expose a hollow interior, showing a number of spaced holes formed therein, and showing an acetabular component mounted in the lip that is also hollow and includes a number of holes formed therein and showing tubes connected to pass a chemical agent into the hollow stem and acetabular member;

FIG. 16 is a side elevation view of a general outline of a patient's penis and scrotum showing a penile implant therein extending the length thereof that includes a number of longitudinally spaced holes and is connected through a tube to a reservoir and showing a hypodermic needle as a pump; and FIG. 17 is a graph comparing the blood levels present in sheep over time of the antibiotic Gentamicin administered by IV dose, cement dose, and device dose, in a sheep study.

DETAILED DESCRIPTION

In a practice of surgical procedures where a component or device or devices are installed in a human body, the occurrence of an infection at the site of such procedure is a serious complication. In the past, to eradicate bacterial infections, the patient has often been treated with large doses of antibiotics by mouth or injection. Such treatments themselves have often had serious side effects with such treatment sometimes being unsuccessful and requiring that the site be reopened and treated. The present invention provides a system of various configurations of a sump or bladder that is shaped to fit between a prosthesis and bone surface or is to be positioned adjacent to a bone or trauma site that is involved in a surgical procedure. Thereat, the individual sump or bladder is then used to dispense an antibiotic or like chemical agent through holes or pores formed therein. The chemical agent is delivered to the sump or bladder through a tube that passes under the patient's skin and connects to a reservoir with a pump arrangement. With the system installed, a surgeon or other medical practitioner can pass, from or through the reservoir, a measured flow of a chemical agent directly to the surgical site, thereby medicating only the area of concern rather than the whole body. Such treatment increases the effectiveness of such medication, decreases the potential for unwanted side effects and minimizes the likelihood of infection, and is useful to quickly control any infection as develops. Additionally, within the scope of this disclosure, the system can be employed for dispensing other liquid chemical agents to a surgical site, such as a chemical agent for controlling pain, chemical agents to degrade bacterial cells, chemical agents to stimulate growth, or chemical agents to kill unwanted cells, such as tumor cells.

In FIG. 5 is shown a distal femur 11 and proximal tibia 12 of a patient's knee 10. Which distal femur and proximal tibia are shown as having been shaped, as by sawing off sections from the femoral condyles and the proximal tibial plateau, shown as surfaces 11a and 12a, respectively, that are to receive, respectively, a femoral component 13 and a tibial component 14 of a prosthetic knee, that is secured to prepared surfaces 11a and 12a. During which prosthesis component mounting, sumps or bladders 15 and 16 of the chemical dispensing system of the invention, shown also in FIGS. 1 through 4, are arranged between the respective bone ends 11a and 12a and the prosthetic undersurfaces, as shown in broken lines in FIG. 5.

Figure 4:
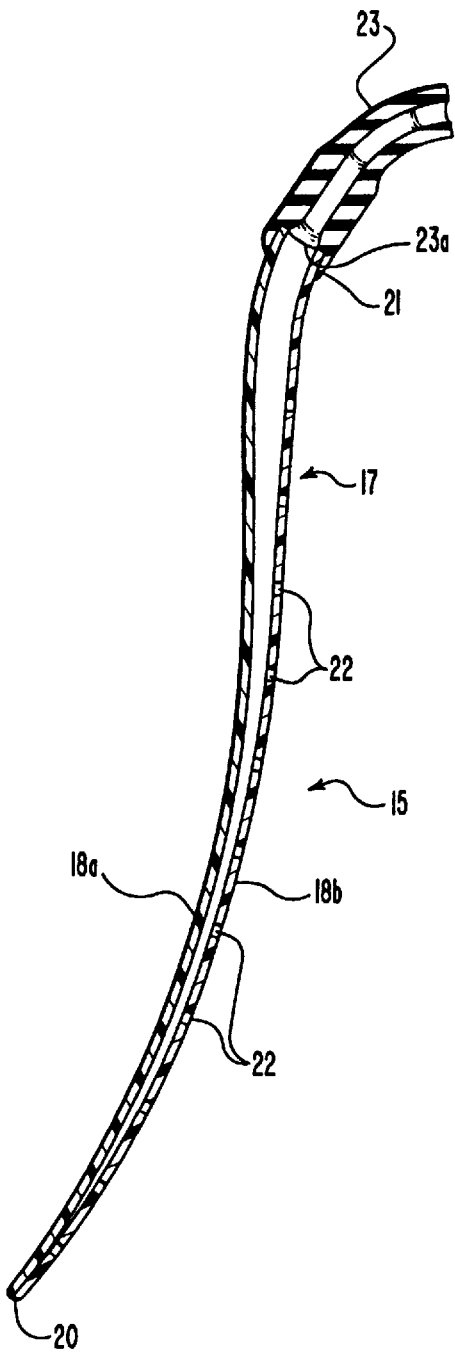
FIG. 4 is a profile sectional view taken along the line 4—4 of FIG. 2.

The sumps or bladders 15, as shown in FIGS. 2, 4 and 5, are a pair of essentially identical flat sleeves 17 that each have top and bottom sections 18a and 18b, respectively that are joined along their outer edges 19 as by heat welding, an adhesive bonding, or the like. Both the bladders 15 are closed at their forward ends 20, shown herein as pointed ends, and are necked into a sleeve 21 in their rear ends. The top and bottom sections 18a and 18b are shown in FIG. 4 as formed from a thin plastic material that is preferably biodegradable to be absorbed by the body during the healing process. For which manufacture any number of biocompatible materials such as silicone, polyurathane or polylactic acid can be used satisfactorily for both of the bladders 15 and 16 as well as the other flexible sump or bladder arrangements as set out hereinbelow.

Shown in FIGS. 2, 4 and 5, the sumps or bladders 15 top section 18a, which is the surface that is in contact with the prosthesis undersurface, is a flat section with no holes therein. Additionally, a prosthesis itself can be formed to contain the sump or bladder, within the scope of this invention. For the sump or bladder 15, the bottom section 18b includes a number of spaced holes 22 formed therein that are of a size to dispense a slow flow of a chemical agent therethrough, that chemical agent bleeding onto the prepared bone surface 11a. Which holes 22 of the sump or bladder 15 and the other sumps or bladders of the other embodiments, to provide such slow flow are formed to allow the chemical agent introduced into the sumps or bladders 15 to flow throughout the cavity to be dispensed over most if not all of the bone end surface 11a.

To provide for passing a chemical agent, which may be an antibiotic, pain inhibiting chemical, chemical agent to degrade bacterial cells, chemical agents to stimulate growth, or chemical agent to kill unwanted cells, such as tumor cells, or the like, or a combination thereof, into the sumps or bladders 15, the sleeve 21 end thereof receives an end 23a of a tube 23 fitted therein. Which tube 23, as shown in FIG. 4, is preferably formed from a plastic material that is flexible. The tubes 23 that extend from each sump or bladder 15, as shown best in FIG. 2, are joined at a Y junction 24 into a single tube 25 that is preferably also formed from a flexible plastic material. The tube 25 provides for passing a chemical agent from a reservoir and pump arrangement, as set out and described hereinbelow. Also, to facilitate maintaining the sumps or bladders 15 to the prepared distal femur surfaces, holes 26 are provided at spaced intervals along the edges 19 through which a suture may be passed in order to anchor the device in place on the bone surface 11a.

Figure 3:
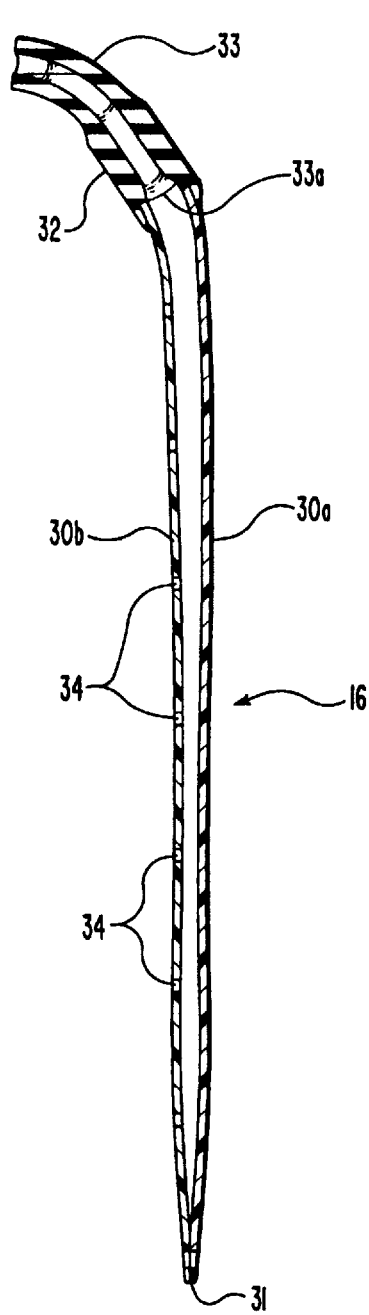
FIG. 3 is a profile sectional view taken along the line 3—3 of FIG. 1.

FIGS. 1 and 3 show the sump or bladder 16 arranged between the tibial prosthesis component 14 and the prepared flat end surface 12a of the proximal tibia 12 shown in broken lines in FIG. 5. The sump or bladder 16, like the sumps and bladders 15 described above, is preferably formed by joining top and bottom sections 30a and 30b, that are essentially ovals, and are joined around their edges 31. Shown in FIGS. 1 and 3, a portion of edge 31 is formed into a sleeve 32 that, like sleeve 21 of the sumps or bladders 15, is for receiving an end 33a of a tube 33 fitted therein, as shown best in FIG. 3, that extends from the proximal femur surface 41. The tube 33 like tube 23 is for passing a chemical agent into the annular space between the top and bottom sections 30a and 30b. Also, like the bottom section 18b of the sumps or bladders 15, the bottom section 30b that, as shown in FIG. 5, is positioned opposite to the proximal tibial flat surface 12a and includes a number of spaced holes 34, shown in FIG. 3, formed therein. The holes 34 are preferably like the described holes 22 and are for passing a low volume flow of a chemical agent therethrough onto the bone surface 12a. Which chemical agent will have traveled through the tube 33 from a reservoir and pump arrangement, 62 as shown in FIG.

1 as set out and discussed hereinbelow with respect to FIG. 6. Further, like the holes 26 formed at spaced intervals in the edge 19 of the sumps or bladders 15, the edge 31 of the sump or bladder 16 preferably also includes spaced holes 35 formed therealong. The holes 35, like holes 26, are for passage of a suture, or the like, therein in the process of fitting the sump or bladder 16 onto the bone surface 12a, as discussed with respect to the sumps or bladders 15.

In FIGS. 6 and 7 are shown another arrangement of a chemical dispensing system of the invention for use as a replacement prosthesis in a total hip replacement procedure where a patient's hip socket and ball end of their proximal femur are replaced with a prosthesis. To provide for installing the prosthesis the femur 40, at its proximal end, has its head and neck removed along a line between the greater and lesser trochanters, leaving a surface 41, and exposing the intramedullary canal 42. Shown in broken lines, the intramedullary canal 42 is prepared adjacent to the surface 41 and therealong, as by appropriate shaping, to receive a femoral component 43 of a hip prosthesis fitted therein.

Shown in FIG. 6, the femoral component 43 includes a body portion 44 with a stem 45 extending therefrom, shown in broken lines, that are fitted in the prepared intramedullary canal 42 end exposed in the surface 41. The femoral component 43 further includes a neck section 46 that extends outwardly from a surface of the body portion 44. The neck section 46 mounts to a hemispherical section 47 as a ball end thereof that is for fitting into a concave depression on socket 49 formed in the hip 48, as set out below. The portion of intramedullary canal 42 adjacent to the stem 45, and the stem surface, as appropriate, are formed to accommodate a sump or bladder 50, shown in broken line, fitted alongside the stem 45. The sump or bladder 50 is preferably a tube that is formed of a thin flexible biocompatible material, and, like the sumps and bladders 15 and 16, is possibly formed from a biocompatible or biodegradable material to be absorbed by the human body over time. The sump or bladder 50 is closed across a lower end 51 and includes a number of spaced holes formed therein that are of a diameter to accommodate a low volume passage of a liquid chemical agent passed into the tube through a neck end 52 whereto is fitted a tube 53. Such chemical agent is passed through the tube 53 from a reservoir and pump arrangement, as set out below.

A chemical agent, as for example, an antibiotic, topically applied anesthetic and/or the like, or a combination thereof, can, at appropriate time intervals, as selected by a surgeon/operator, be passed into the sump or bladder 50 to travel into the adjacent bone material. Similarly, the concave cavity 49 that is formed into the patient's pelvis 48, and replaces their acetabulum, receives an acetabular cup component 53 secured in the concave depression 49. The cup component 53 is to receive the hemispherical section 47 secured to the neck 46 seated therein. For the invention, a cup component sump or bladder 54 is provided that includes a center cavity 56, shown as a space between an outer surface 55 and an inner surface 55a, shown in broken lines. Large holes 57 are provided through both the outer and inner surfaces for receiving fasteners, not shown, such as screws or sutures, that have been passed through the cup component 53 for mounting the component in the concave depression 49. The small holes 58 are shown formed through the outer surface 55 that, like the holes formed through the sump or bladder 50, are for slowly passing a chemical agent introduced from the center cavity 56 into the surrounding bone material of the hip 48. To pass such chemical agent into the cavity 56 the cup component sump or bladder 54 includes a neck 59 which extends beyond the hip bone surface and receives a tube 60 connected thereto. The tubes 53 and 60 are shown broken with a single tube 61 extending from a junction of which tubes 53 and 60, which tube 61 connects to a reservoir and pump arrangement, shown at 62 and described later herein, 62 for passing a chemical agent therefrom, as set out below.

It should, however, be understood that the necks 52 and 59 of the respective tube 50 and cup component sump or bladder 54 are preferably arranged to allow for release of the tubes 53 and 60, allowing them to be pulled out of the patient after healing. Accordingly, it should be understood, the described cup component sump or bladder 54 is preferably formed from a thin biocompatible material for positioning between a conventional acetabular cup component of a hip prosthesis and the bone surface of the concave depression 49 formed in the hip 48 to function like the sumps or bladders 15 and 16 set out and described above. Which material, like that utilized for bladders 15 and 16, is potentially biodegradable to be absorbed by the body in the healing process.

FIGS. 1 and 6 show an embodiment of a reservoir and pump 62 that, as shown also in FIG. 14, may, like the reservoir 150 set and described hereinbelow with respect to FIG. 16, be arranged as an external device on a fixation device 120. Shown in FIGS. 1 and 6, the reservoir and pump 62 include a housing 140, shown as having a flattened cone shape that contains a center cavity, not shown, and maintains a piston 142 slidably fitted in the center cavity. The piston is arranged to move up and down therein opposed by a spring biasing, not shown, to apply positive pressure to a fluid contained in which center cavity. The pumping action is provided by an operator, not shown, pushing a top surface 143 of which piston 142. The housing 140 is formed into a neck 144 extending outwardly from a point along its lower edge and ends in a sleeve 145. The sleeve 145 receives the tube 61 fitted therein for transferring the chemical agent into lines 53 and 60, as described above.

As an alternative to the sumps or bladders for use with the components of a hip prosthesis, as described above, FIG. 15 shows an embodiment of a chemical dispensing system for use as a temporary hip prosthesis for temporary placement in the patient's proximal femur 40 and hip 48, as shown in FIG. 6, to deliver a chemical agent into the surgical site to eradicate a bacterial infection whereafter the temporary hip prosthesis of FIGS. 15 is replaced with a permanent prosthesis. Like a fitting of the prosthesis of FIG. 6, the patient's proximal femur, as shown, will have been cut to have flat surface 41 and has had its intramedullary canal 42 shaped to receive, fitted therein, a stem 70 of a femoral component 68 of the temporary hip prosthesis. The femoral component 68 includes a body 69 wherefrom a neck 72 extends that mounts a hemispherically shaped ball end 73. Unique to the femoral component 68 is that it is formed, as shown in a broken away portion to have a hollow compartment formed adjacent to its outer surface that includes an number of spaced small diameter holes 72 formed through the stem 70 thereof. The holes 72 are of a diameter to provide a low volume flow of a chemical agent under pressure therethrough, functioning like the holes formed through the above described sumps or bladders, to dispense a liquid chemical agent onto a bone material.

Like the femoral component 68, the temporary hip prosthesis of FIG. 15 includes, a temporary acetabular member 75, that is for fitting in the cup 49 formed in the hip bone 48, and is formed to dispense a chemical agent therefrom into the bone material of cup 49. Accordingly, the acetabular member 75 includes outer and inner surfaces 76 and 76a, respectively, with a space or cavity 77 formed therein adjacent to the outer surface 76. As shown, the outer surface 76 includes a number of spaced small diameter holes 78 formed therethrough. The holes 78, like holes 72 of the temporary femoral member 68, are for passing a low volume of a liquid chemical agent therethrough.

To provide a flow of the liquid chemical agent to the respective temporary component 68 and member 75, each includes a portal 68a and 75a, respectively, whereto tubes 79 and 80, respectively, are connected. The tubes 79 and 80 are joined into a single tube 82 at a Y junction 81. The tube 82, in turn, may be connected to a reservoir and pump arrangement 62, as shown in FIG. 6, or to the reservoir and pump 150 of FIG. 16, within the scope of this disclosure, for passing a flow of a selected chemical agent therefrom.

Additional embodiments of chemical dispensing systems that are for use in other orthopedic surgical procedures, are shown in FIGS. 8, 9 and 10. Therein, a chemical agent dispensing rod or nail 85 is shown positioned in an intramedullary canal of a bone, across a fracture therein. A sump or bladder 100 is provided for fitting in the nail's longitudinal cavity 88, to be opposite to the site of the fracture shown in FIGS. 9 and 10 as bone fragments 97. Further, another embodiment of a nail 105 that is for use like the nail 85, of FIG. 9, is shown in FIGS. 11 through 13. Which nails 85 and 105, as described below, each provide for dispensing a chemical agent passed thereto to the bone fracture from a reservoir and pump arrangement, as described above.

FIG. 8 shows nail 85 formed from a solid rod section 86 and is bent from its longitudinal axis at 87. Which bend 87, as shown in FIG. 9 is to conform to the shape of a intramedullary canal 96 of a tibia 95 that has been reamed out therealong, as necessary, to accommodate the nail 85 fitted therein. Though, it should be understood, a nail like nail 85 of an appropriate geometrical design could similarly be used to fit in the intramedullary canal of the femur or humerus, within the scope of this disclosure.

As shown in FIG. 8, the nail 85 includes a center longitudinal cavity 88 and is bent at 88a proximate to its proximal end, to accommodate and allow for passage of a bladder 100, when such is used, as shown in FIG. 10, fitted therethrough. The cavity 88 connects, at its proximal end to a fitting 89 and is closed at 88b above the nail distal end. A number of transverse holes 90 are formed through the nail that are parallel and spaced apart along the nail midsection and pass through the nail cavity 88. Accordingly, without bladder 100 fitted therein, when a liquid chemical agent is passed through a tube 91 that connects to the fitting 89, that fluid will pass directly out of the transverse holes 90 and into the surrounding bone material.

FIG. 9 shows the nail 85 as spanning a fracture in the bone 95, with several bone pieces 97, as shown in FIGS. 9 and 10, at the fracture location. So arranged, it may be desirable to confine dispensing of the chemical agent, that can be an antibiotic, topical anesthetic, growth agent, or the like, or a combination of chemical agents, into the area of the fracture only. To so direct a flow of chemical agent into the fracture, FIG. 9 shows a preferred location of the bladder 100, and FIG. 10 shows the bladder 100 arranged in the nail cavity 88 such that it is opposite to the fracture after it has been slid therealong. Which bladder 100, as shown, for maintaining it at its location, may include an upper plug portion 101 that is effectively a sleeve 101 with a center wall 102 arranged across which sleeve enclosing the space therebetween. A wall 102a of sleeve 101, below an end 101a thereof, that connects to the center wall 102 to complete the cavity such that an open center longitudinal space 103 is opposite to the fracture. The space 103, as shown, terminates in a bulbus end 103a that will expand to engage and seal against the nail cavity 88 wall when fluid, under pressure, is passed thereto. Further, to guide travel of the bladder along the nail cavity 88, a pointed end 104 is preferably provided as the bladder distal end. The bladder walls 102 and 102a, and end 104, as shown, are preferably formed of a biocompatible material, with the holes 105 formed through which walls 102 and 102a of a diameter to pass a low volume flow of a liquid chemical agent therethrough that travels into the nail's transverse holes 90 and out into the site of the fracture, shown as bone fragments 97.

Shown in FIG. 10, with an introduction of a liquid chemical agent from a reservoir and pump arrangement through tube 91 and into the bladder 100, the center wall 102 will flex outwardly, illustrated by arrow A, to engage and seal against the opposing inner wall of sleeve 101. Which sleeve 101 outer surface will itself be urged outwardly sealing against the nail cavity 88 wall, prohibiting a flow of the chemical agent therebetween. So arranged, with the bulbus end 103 expanded, as described above, seals off the bladder lower end to the nail cavity 88 wall, and with the expanded sleeve 101 sealing against the nail cavity wall thereabove. The cavity formed by the center wall 102 and sleeve wall extension 102a thereby contains the chemical agent under pressure. So arranged, the holes 105 through the sleeve wall extension 102a directs the flow of chemical agent through the nail transverse holes 90 that are opposite to the area of the fracture, shown at 97.

It should, however, be understood that a sump or bladder 100 without the upper plug portion 101, center wall 102 and bulbus end 103a and pointed end 104 could be employed to travel into the nail cavity 88 to dispense a liquid chemical agent into the fracture, within the scope of this disclosure. Also, it should be understood, the above described arrangements could be employed with tibial, femoral and humeral nails, within the scope of this disclosure except that the geometry of the particular nail would influence the sump or bladder configuration. Additionally, to provide for closing off the nail cavity 88 below the sump or bladder lower end, a spacer 100a, shown in FIG. 10, can be fitted into the nail cavity 88 to be just below a fracture site when the nail is fitted into the patient's intramedullary canal.

Another embodiment of a sump or bladder 110 of the invention for dispensing a liquid chemical agent into a section of bone material is shown in FIGS. 11, 12 and 13. As with the above described sump or bladder 100, the sump or bladder 110 is for use with an intramedullary nail 105, shown herein as a conventional intermedullary nail, that is bent from the vertical at 106, has a clover leaf cross section, is open longitudinally at 107, and includes a straight longitudinal slot 108 formed therein. Further, as shown in a nail embodiment of FIG. 13, the lobes of the clover leaf cross section, at a location therealong that will be adjacent to a bone fracture 85a preferably include a number of spaced holes 109 formed therethrough.

An introduction of a chemical agent 111, under pressure, into bladder 110, as shown in FIG. 12, causes a flow, shown as drops 111, of the chemical agent, to pass through a hole 112 in which bladder 110 and travels through the longitudinal slot 107 onto the bone 85 at break 85a. Alternatively, for the arrangement of FIG. 13, where the nail 105 lobes include holes 109, the bladder 110 preferably includes a number of spaced holes 112 formed therein. The spaced holes 112 provide for passing the liquid chemical agent therethrough and out of the nail holes 109 to coat the bone surface around the nail 105, functioning like the nail and sump or bladder arrangement of FIGS. 8 through 10.

Optionally, like sump or bladder 100 described above with respect to FIG. 10, the sump or bladder 110 may include an arrangement for sealing the top and bottom thereof within the nail longitudinal cavity for containing the flow of chemical agent to a desired bone site or location. To this end, as shown in FIG. 13, the sump or bladder 110 includes a pointed distal end 113, that may appear like and function like the sump or bladder end 104, as described above. Also, to provide for sealing the sump or bladder top or proximal end within the nail longitudinal cavity, an expanding collar 114 may be included around the bladder top end that has a capability for expanding into engagement with the longitudinal cavity wall. The sump or bladder 110 can thereby be sealed at an appropriate location along the nail 105. Also, prior to fitting the sump or bladder 110 into the nail 105, as shown, a spacer, as described above but not shown, can be fitted there for blocking off the nail cavity above the fracture to direct the liquid chemical agent flow into that fracture FIG. 14 shows still another arrangement of a chemical dispensing system that is incorporated into a fracture external fixation device 120, hereinafter referred to as fixation device. Fixation device 120 is for use in maintaining the positioning of ends of a bone 85 such that ends of a fracture 85a therein are maintained together. The fixation device 120 of the invention provides for immobilizing the bone 85 during healing and additionally provides for dispensing a chemical agent, as described above with respect to the other described embodiment of the chemical dispensing system, into and onto the bone above and below the fracture 85a. As with like conventional fracture fixation devices, the fixation device 120 includes a pair of blocks 121a and 121b that mount to ends of a rod 122. Preferably, the distance between the blocks 121a and 121b is adjustable, and accordingly, the rod 122 is shown to be threaded for turning into or out of threaded holes formed through which blocks. Or, within the scope of this disclosure, another arrangement for adjusting the spacing distance could be utilized. Also, within the scope of this disclosure, the described arrangement could be employed with another fracture fixation device, such as an Ilizarov type external fixation device, or the like.

A pin 123, that is shown in use in FIG. 14 and has been removed out from a block and enlarged in FIG. 14A, is provided for fitting through a hole in a block 121a and 121b, each pin to be parallel to the other pin and at a right angle to the rod 122. Each pin 123 is for fitting through a block and locking therein, as by turning a set screw through a block wall to engage the pin side, not shown, or other like arrangement can be so used. A screw end 124a is formed as a forward end thereof of each pin 123 that is for fitting through an incision in the patient's skin 85b and turning into the bone 85, as shown in FIG. 14. So arranged, the pins 123 maintained in the blocks 121a and 121b hold the bone ends at break 85a together during healing. To discourage an occurrence of infection during which healing, to treat an established infection, or to promote bone healing, the invention provides for dispensing a chemical agent, such as an antibiotic, or growth factors, or the like, through longitudinal passages 125 of a cylindrical body 124 of each pin, shown in broken lines in FIG. 14A, through an axial hole 125a pin body screw end 124a and/or out transverse holes 125b formed through the screw end 124a, and travels into and onto bone 85, above and below the break 85a.

To provide for passing a chemical agent through each pin body 124, a pin body end 124b opposite to its screw end 124a, as shown in FIG. 14, receives an end of a tube 126 fitted thereon whose opposite end connects into a pump and reservoir 127 to receive a flow of a selected chemical agent therefrom. Which pump and reservoir 127 is like the described pump and reservoir 62 of FIG. 6 or may be the pump and reservoir 150 of FIG. 16, and reference is hereby made to the discussion of which pump and reservoirs 62 and 150 set out below.

FIG. 16 shows still another arrangement of a chemical dispensing system of the invention that is for arrangement with a penile implant 130. The penile implant 130, as shown, is for fitting into an incision made in a patient's penis 129 during a surgical procedure thereon. Which penile implant 130 is essentially a balloon 131 that is fitted into a longitudinal cavity formed in the patient's penis 129 and connects, at a neck end 131a, to a hose or tube 132 that extends out from the penis and connects to a bulb type air or fluid pump 133, or the like. In use, a patient wishing to erect his penis fills the balloon 131 with air or fluid by squeezing the bulb pump 133 between his fingers, filling the balloon.

As with the other surgical procedures practiced, as described above relative to the other Figures, post surgical infection is also a serious problem in a penile implant procedure. To discourage such infection or to treat an established infection, a sump or bladder 134 of the invention is attached to the balloon 131, along the length thereof, that includes a number of longitudinally spaced holes 135 wherethrough a chemical agent will pass at a low volume flow rate into the tissue around the implant. As with the earlier described sumps or bladders of the invention, the sump or bladder 134 has a cavity therein and is secured to an end of a tube 136 at a neck end 134a thereof. Which tube 136 connects on one end to the neck end 134a and has its other end fitted to a reservoir and pump 150, that is another embodiment of a reservoir and pump arrangement for use with the invention, and is described in more detail hereinbelow. It should, however, be understood that the reservoir and pump arrangement 150, and the earlier described reservoir and pump arrangement 62, are examples only of apparatus for passing a liquid chemical agent to a sump and bladder arrangements, as set out herein, and that other reservoir and pump arrangements could be so utilized within the scope of this disclosure.

FIG. 16 show reservoir and pump 150 as an implantable device having a body 151 that has a cavity therein, not shown, that is disposed below a pad 152 formed as a body top surface. The pad 152 is preferably formed from a section of a rubber, or like material, to pass and seal around a needle 154 of a hypodermic 153, and to reseal when the needle is removed. In practice, a pressurized flow of a liquid chemical agent is passed through tube 136 that connects through a sleeve 157 of a neck 156 formed in the body 151 to the cavity. A surgeon/operator inserts the needle 154 pointed end through the pad 152 and into the cavity that may already have a volume of the liquid chemical agent therein. Thereafter, by depressing the hypodermic 153 plunger, not shown, a flow of the liquid chemical agent is passed in the cavity, urging a flow of the liquid chemical agent therefrom that passes through the tube 136 to the sump or bladder 134, as described above.

Hereinabove have been set out a number of different arrangements of chemical dispensing systems that each include at least one sump or bladder formed to be positioned immediately adjacent to a site of a surgical procedure. Each sump or bladder is provided for dispensing a low volume flow of a chemical agent that it receives into the site through a tube that extends from the sump or bladder and connects to a reservoir and pump arrangement. Common to the different sump or bladder arrangements, as set out herein, is that each includes a vessel that contains a cavity with holes formed through a vessel surface to pass a low volume flow of a liquid chemical agent. Which sump or bladder can be formed for fitting between a prepared bone end and a prosthesis component, as for example, a knee prosthesis component, is preferably formed from flexible material to be flat and may be formed from a material to be absorbed by the body during healing.

FIG. 17 summarizes the results of an animal study conducted on six (6) sheep to compare presence in each animal's blood of an effective but highly toxic antibiotic, Gentamicin, that, as shown, was administered intravenously, as mixed with polymethylmethacrylate applied onto a prepared bone surface, and utilizing the present invention. Gentamicin is a powerful and very effective antibiotic which has been routinely used in a systemic fashion, usually through IV dosing, but is, unfortunately, a highly toxic drug to several systems in the body, specifically the kidneys and ears. As such, its use is limited by considerations for adverse reactions. Accordingly, Gentamicin was a excellent antibiotic to study for determining how the systemic blood levels of the drug varied with different dosing techniques.

From the graph of FIG. 17, it is clear that the sheep who received IV dosing had widely varying blood levels of Gentamicin presence. Such would also produce wide variations in concentration in the kidneys and ear as could lead to complications. Whereas, the consistently low blood levels of Gentamicin shown in the sheep that received the same dosage of Gentamicin utilizing the chemical dispensing system of the invention show that very little of the Gentamicin passed out of the muscle and bone into the circulatory system, which amount that did escape would not produce a toxic dose to either the kidneys or ears. Similarly, the sheep who received Gentamicin by incorporating it into bone cement that was then placed in the joint registered no active Gentamicin in their circulatory system and were accordingly graphed as part of the graph X-axis.

Additional to the presence of Gentamicin in the animals blood, another concern of the study was to demonstrate that Gentamicin delivered locally, as provided by the present invention, would diffuse from the site of the injection into the surrounding tissue in a timely and effective manner. To document diffusion, a radionuclide solution was mixed with a dose of Gentamicin that was delivered locally. A bone scan was conducted three hours after the dose was given into the knee. The bone scan showed a zone of diffusion that measured to sixteen (16) centimeters from top to bottom by thirteen (13) centimeters from front to back. To further document that the Gentamicin had indeed spread from the joint into surrounding tissues, a biopsy sample was taken from a muscle that was six (6) centimeters from the joint line (the site of delivery). This tissue was taken from the same location in each of the sheep samples. Each muscle was then weighed and one hundred twenty (120) grams of its was diluted with a twenty eight percent (28%) saline solution by weight and was liquified in a blender. The resulting fluid was then tested for Gentamicin levels. Even though the Gentamicin was diluted significantly by the saline, tissue concentrations were still found to be ten point five (10.5) micrograms/ml and five point nine (5.9) micrograms/ml respectively in the sheep whose Gentamicin was delivered with the present invention. Which concentrations are considered to be therapeutic doses of Gentamicin. The sheep that received intravenous Gentamicin and Gentamicin mixed in bone cement has tissue concentrations of Gentamicin of zero micrograms/ml.

From the results of the three studies set out above, it is clear that the chemical dispensing system of the invention is an extremely effective system for delivering Gentamicin to a site of infection. From the data, it is clear that delivery by the present invention creates very high concentrations of antibiotic in a defined region, and that most of the antibiotic will remain in the local area with very little escaping into the animals' central circulation as could produce adverse effects elsewhere in the body. It is believed, based on the results set out above, that these results would likely be duplicated with any other liquid medication as the present invention is suitable for use with.

While preferred embodiments of our invention in a chemical dispensing system and its use have been shown and described herein, it should, however, be understood that the present disclosure is made by way of example only and that variations to the embodiments as described are possible within the scope of this disclosure without departing from the subject matter coming within the scope of the following claims and a reasonable equivalency thereof, which claims we regard as our invention.

We claim:

1. A chemical dispensing system to provide a low volume flow of a chemical agent to a surgical site comprising, a bladder means having a cavity therein that is closed at a distal end and attached at its proximal end to one end of an open tube means; a means connected to said open tube for supplying a flow of said chemical agent into said open tube to pass into said bladder means cavity wherein the bladder means is a pair of thin sections of a flexible material each formed to a shape of a prepared bone surface and are joined along their common edges, one of which said thin sections of material is for positioning over the prepared bone surface and has at least one hole formed through at least one bladder surface opposite to said prepared bone surface; and a proximal end of which said joined thin sections is formed into a neck that is open therethrough for receiving an end of the open tube fitted therein.

2. A chemical dispensing system as recited in claim 1, wherein the thin sections are a flexible biocompatible material that will be broken down by the body during a healing process.

3. A chemical dispensing system as recited in claim 1, wherein the means for supplying a flow of a liquid chemical agent into the open tube is a body having a cavity therein that is open into a neck means for coupling to an end of said open tube; and means for passing said liquid chemical agent, under pressure, into said body cavity.

4. A chemical dispensing system as recited in claim 3, wherein the means for passing the liquid chemical agent, under pressure, into the body cavity is a pump means connected into said body cavity to be manually operated to apply a pressure to a volume of said liquid chemical agent contained in said body cavity.

5. A chemical dispensing system as recited in claim 3, wherein the means for passing the liquid chemical agent, under pressure, into the body cavity is a hypodermic having a hollow needle with a pointed end; and a membrane is arranged in the body across an opening into the body cavity that the needle pointed end is passed through, the membrane to seal around said needle, and to reseal itself when said needle is withdrawn.

* * * * *